United States Patent [19]

Buettner et al.

[11] Patent Number: 5,998,589
[45] Date of Patent: Dec. 7, 1999

[54] METHOD OF PURIFYING HUMAN FACTOR VIII

[75] Inventors: Joseph A. Buettner, Raleigh; June P. Davis, Cary, both of N.C.

[73] Assignee: Bayer Corporation, Pittsburgh, Pa.

[21] Appl. No.: 09/350,605

[22] Filed: Jul. 9, 1999

Related U.S. Application Data

[62] Division of application No. 09/146,402, Sep. 3, 1998.
[51] Int. Cl.$^6$ .............................. C07K 17/00; C07K 17/02
[52] U.S. Cl. ......................... 530/413; 530/412; 530/425; 530/429; 530/829; 436/161
[58] Field of Search ..................................... 530/412, 413, 530/425, 829; 436/161

[56] References Cited

U.S. PATENT DOCUMENTS 5,133,866   7/1992   Kauvar ..................................... 210/635
5,834,318   11/1998  Buettner .................................. 436/518

*Primary Examiner*—F. T. Moezie
*Attorney, Agent, or Firm*—Huw R. Jones

[57] ABSTRACT

The invention is a method of purifying Factor VIII comprising the steps of contacting a solution containing Factor VIII with a Factor VIII-binding substrate under conditions sufficient to bind Factor VIII to the substrate, wherein the Factor VIII-binding substrate comprises one or more peptides bound to the substrate, wherein the peptides are selected from the group consisting of SEQ ID NO:1, SEQ ID NO:2, and SEQ ID NO:3, and then eluting the bound Factor VIII.

1 Claim, 8 Drawing Sheets

Western Blot

Gel, silver stained

METHOD OF PURIFYING HUMAN FACTOR VIII

CROSS REFERENCE TO RELATED APPLICATIONS

This application is a division of U.S. Ser. No. 09/146,402 filed Sep. 3, 1998, now pending.

BACKGROUND OF THE INVENTION

1. Field

This invention is generally directed to identifying protein-ligand interactions, and specifically with peptide ligands which bind human Factor VIII and which may be used in a process for the affinity purification of human Factor VIII.

2. Background

Human Factor VIII, (antihemophilic factor; FVIII:C) is a human plasma protein consisting of 2 polypeptides (light chain molecular weight of 80,000 daltons and heavy chain molecular weight variable from 90,000 to 220,000). It is an essential cofactor in the coagulation pathway; required for the conversion of Factor X into its active form (Factor Xa). Factor VIII circulates in plasma as a non-covalent complex with von Willibrand Factor (aka FVIII:RP). Blood concentrations of Factor VIII below 20% of normal cause a bleeding disorder designated hemophilia A. Factor VIII blood levels less than 1% result in a severe bleeding disorder, with spontaneous joint bleeding being the most common symptom. Factor VIII can be isolated from either a plasma derived source (cryoprecipitate) or from a genetically engineered recombinant source. Recombinant DNA technology has allowed construction of plasmids that direct the expression of fusion products of Factor VIII protein in transfected mammalian cells (See U.S. Pat No. 4,757,006).

Several methods have been described for purification of Factor VIII from plasma sources. Tuddenham et al. disclose a method for separating FVIII from human plasma by immunoabsorbent chromatography (Tuddenham, et al., *J. Laboratory Clin. Med.*, (1979), 93:40–53). The method involved using rabbit anti-FVIII:C polyclonal antibodies adsorbed to agarose beads, and desorption using a calcium gradient. Notably, it was sufficiently selective to distinguish FVIII:C from FVIII:RP. D.E.G. Austen demonstrated another technique using ionexchange chromatography on amino-hexyl-substituted agarose beads (Austin, D.E.G., *British J. Heamotol.*, (1979), 43:669–674). However, it has been reported that both methods suffer from some level of contamination of the resulting FVIII:C by FVIII:RP.

Zimmerman, et al., U.S. Pat. No. RE32011 disclose a human monoclonal antibody-based immunoaffinity two-step purification procedure. The first step is adsorption of the FVIII:C/FVIII:RP complex from a human plasma source, followed by a buffer wash, and subsequent desorption of FVIII:C using a calcium solution that elutes only FVIII:C (FVIII:RP remains bound). The second step is concentration of the FVIII:C by adsorbing the eluate from step one to an aminohexyl-substituted agarose column with a subsequent calcium buffer wash. This results in a concentration of FVIII of over 160,000-fold from plasma.

Several purification schemes utilize antibody affinity columns. Wood, W., et al., *Nature*, (1984), 312:330–337 demonstrated another immunoaffinity purification, using the C7F7 MAb which is specific to the FVIII:C 80kD fragment. Rotblat, F., et al., *Biochemistry*, (1985), 24:4294–4300 also describe an immunoaffinity purification of FVIII:C of over 300,000-fold from cryoprecipitate by polyelectrolyte purification, followed by affinity separation of a sepharose-anti-FVIIIR:Ag, and a final adsorption to a FVIII:C specific MAb column. To date, the most successful purifications of Factor VIII from plasma or from recombinant sources have been accomplished by using murine monoclonal antibodies specific to either Factor VIII or von Willibrand Factor (see Zimmerman, et al, supra, U.S. Pat. No. RE32011).

Although monoclonal antibodies have been used successfully to obtain a relatively pure Factor VIII preparation, monoclonal antibodies can be present in the Factor VIII effluent because of leaching from the support matrix. This raises the possibility of antigenicity when the final preparation is introduced into animal systems, since murine monoclonal antibodies have been shown to be antigenic. A second disadvantage of the use of monoclonal antibodies is the requirement of cell culture facilities for producing the antibodies and the concomitant cost of purification and attachment onto a support matrix. And finally, the stability of the antibody binding site may not be amenable to the rigorous conditions necessary to sanitize the column.

Affinity chromatography is one of the most efficient techniques for purifying a protein from a complex mixture. With potential advantages including high stability, efficiency, selectivity, and low price, peptides have been investigated as affinity ligands in the pharmaceutical industry. A recent approach for identifying such ligands is to screen peptides from combinatorial peptide libraries (Baumbach, et al., *BioPharm*, (1992), 5:23–35; Buettner, J., et al., *Int. J. Pept. Prot. Res.*, (1996), 47:70–83; Huang, P., et al., *BiotechnoL & Bioeng.*, (1995), 47:288–297; Huang, P., et al., *Bioorg. & Med. Chem.*, (1996), 4:699–708). It has been shown that by using the "divide-couple-recombine" approach (Furka, et al., Int. *J. Pept. Prot. Res.*, (1992), 37:487–493; Lam, et al., *Nature*, (1991), 354:82–84; Houghten, et al., *Nature*, (1991), 354:84–86), millions of unique peptides of a defined length may be synthesized on resin beads. Each bead contains a unique peptide sequence. These library beads and their corresponding peptide sequences are then exposed to a target protein. Among these millions of peptide sequences, the target protein may bind to several unique bead-sequences. Those beads and their corresponding sequences must be detected, isolated, and identified. Several detection systems, including colorimetric two-step methods (Buettner, et al., (1996), 47:70–83; Houghten, et al. (1991); Lam, et al., *J. Immunol. Meth.*, (1995), 180:219–223) as well as direct fluorescence detection methods (Meldal, et al., Proc. *Nat. Acad. Sci.*, (1994), 91:3314–3318; Meldal, et al., *J. Chem. Soc. Perkin Trans.*, (1995) 1:1591–1596; Needles, et al., *Proc. Natl. Acad. Sci.*, (1993), 90:10700–10704) have been used.

Another method of generating large libraries of peptides for affinity separations is phage display. WO 95/18830, Inhibitors of humanplasmin derived from the kunitz domains, describes the selection of binding domains specific for human plasmin useful as inhibitors, including applications for drugs, for diagnostic reagents and for affinity purification ligands. The claimed binding domains are chimeras of one of the three kunitz binding domains found in lipoprotein-associated coagulation inhibitor (LACI), a 39 kd protein. The binding domains are about 58 amino acids with 7 to 11 amino acid substitutions generated by combinatorial methods. No smaller peptides are used or claimed.

WO 97/35197, Purification of tissue plasminogen activator (tPA), claims binding domains useful for purification of the biological drug tPA, using the same technology as described in WO 95/18830 and WO 97/35196. In this application, the binding domains are 29 amino acids of which 8 were combinatiorialized. One claimed sequence is from a peptide of 11 amino acids, of which 8 residues were derived combinatorially from the binding motifs of the other claimed domains, having the 11-mer sequence: Arg Xaa Cys Xaa Xaa Xaa Xaa Xaa Xaa Cys Xaa. Specific residues are claimed for each position (Xaa) for this presumed cyclic peptide.

It is apparent that other, more specific affinity peptides for binding proteins of biological interest are needed.

SUMMARY OF THE INVENTION

We have discovered a group of small peptides characterized by their ability to bind and purify human Factor VIII. The invention is a composition for binding Factor VIII comprising a peptide having an available Factor VIII binding domain having the sequence of SEQ ID NO: 1, 2 or 3. These peptides bind Factor VIII while the peptide is covalently linked onto a chromatographic support under the conditions described. The sequences of the more preferred peptides having a Factor VIII binding domain are Trp-His-Tyr-Tyr-His-Gly (WHYYHG), His-Ile-Gln-His-Tyr-His (HIQHYH), and His-Gln-Tyr-Gly-Tyr-His (HQYGYH); sequence identification numbers 1, 2 & 3, respectively. The peptides were isolated and identified using a screening process described in U.S. patent application Ser. No. 08/438,331, incorporated herein by reference in its entirety.

The invention also includes a method of purifying Factor VIII comprising contacting a solution containing Factor VIII with a Factor VIII-binding substrate under conditions sufficient to bind Factor VIII to said substrate, wherein said Factor VIII-binding substrate comprises one or more peptides bound to said substrate, wherein said peptides are selected from the group consisting of SEQ ID NO:1, SEQ ID NO: 2, OR SEQ ID NO:3, and then eluting the bound Factor VIII.

DETAILED DESCRIPTION OF THE PREFERRED EMBODIMENTS

Materials

Monoclonal antibodies directed to each hrFVIII chain, polyclonal antisera against the hrFVIII non-expressing BHK cell medium, and an in-process fraction of human Factor VIII (KG2DEAE) were obtained from Bayer Corporation, Biotechnology Division, Berkeley, Cailf. Secondary antibody conjugates and the dye substrates NBT/BCIP and Fast Red were obtained from Pierce Chemical Company, Rockford, Ill. An in-process fraction of recombinant human Factor VIII (KG2DEAE) was obtained from Bayer Corporation, Berkeley, Cailf. FMOC amino acids were from Novabiochem, San Diego, Cailf. All other chemicals were reagent grade or better.

HPLC

The secondary chromatography binding assays were performed upon a Michrom Bioresources HPLC (Auburn, Cailf.). This binary system has the added advantage of a second injection loop which was outfitted with a 5 ml loop. This allowed addition of a third solvent during the HPLC run. Buffer A was 20mM Imidazole, pH=7.0, 10 mM $CaCl_2$, 300 mM NaCl, 0.01% Tween 80. Buffer B is the same as buffer A but with 1M NaCl and 1M $CaCl_2$. Elution buffer (Buffer C) is the same as buffer A but with 40% ethylene glycol monomer and 250 mM $CaCl_2$. Absorbance was monitored at 280 nm.

Library Primary Screen

An assay similar to the one used in U.S. Pat. No. 5,834,318 (incorporated herein by reference) was used to deduce the peptides that bind human Factor VIII. Colorimetric methods are usually based upon a primary antibody and secondary antibody-conjugate system. Antibodies have the potential for being very specific and sensitive. However, antibody-based methods also have the potential for false-positive (yet specific) interactions due to the adsorption of primary antibodies and secondary antibody-conjugates to the peptide library ligand(s) that do not bind the target protein. Therefore, a two-step, subtractive method for identifying peptide ligands from peptide libraries has been developed (U.S. Pat. No. 5,834,318; Buettner, J., 1996, supra). Briefly, the detecting antibody system is contacted with the on-resin peptide library and allowed to adsorb either specifically or non-specifically. The resin is washed to clear unbound detection reagents, then beads that have bound detection reagents are identified by using a blue precipitating substrate. The target protein is then allowed to contact the same library, with subsequent contact with the same detection reagents. This time the target-specific beads are colored red with a precipitating substrate. Red beads are isolated manually and sequenced by classical techniques in the literature (Lebl, et al., *Biopolymers* (*Peptide Science*), (1995), 37:177–198).

Secondary Chromatography Binding Assay

Figure 1:
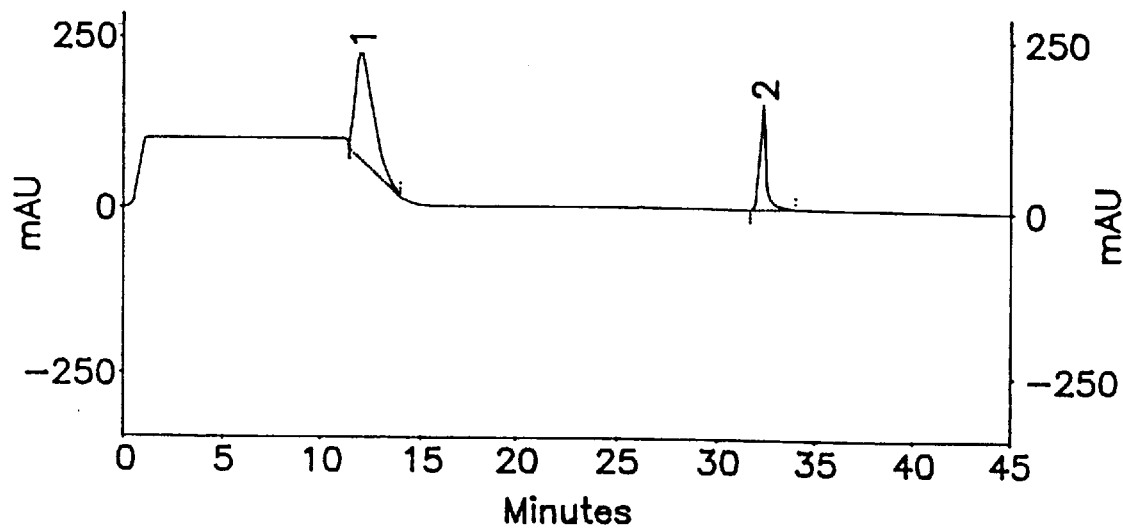
FIG. 1 is a chromatogram showing the elution profile (absorbance at 280nm) of chromatographic separations (secondary binding assay) on the peptide WHYYHG-A-TSK650M (SEQ ID NO: 1).
Figure 2:
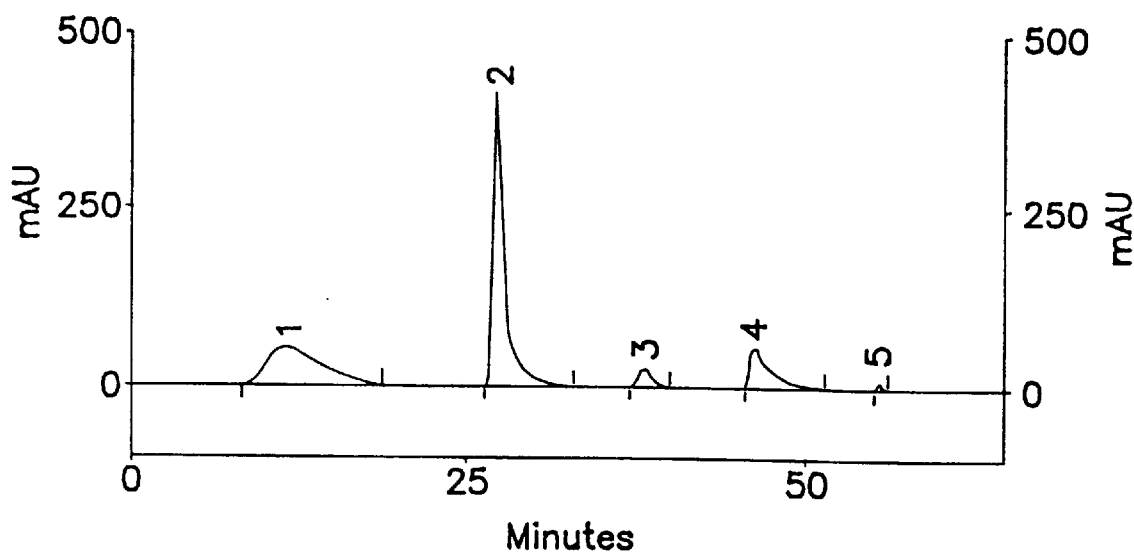
FIG. 2 is a chromatogram showing the elution profile (absorbance at 280nm) of chromatographic separations (secondary binding assay) on the peptide HIQHYH-A-TSK650M (SEQ ID NO: 2).
Figure 3:
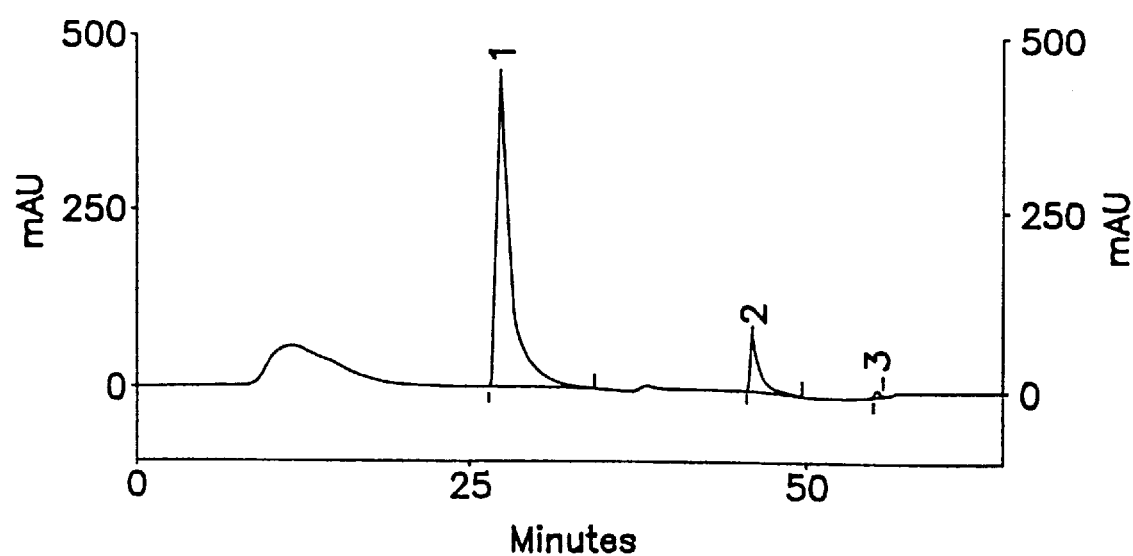
FIG. 3 is a chromatogram showing the elution profile (absorbance at 280nmn) of chromatographic separations (secondary binding assay) on the peptide HQYGYH-A-TSK650M (SEQ ID NO: 3).

Confirmatory FVIII binding assays were performed in a column chromatographic format on the HPLC described above. Batch synthesized peptide-resin (substitution at 100 μmoles/g) was loaded and washed as described in Buettner, J., 1996, supra. The HPLC method injected the sample onto the column at 80 cm/hr linear velocity, allowed for flow-through of unbound protein, then stepped to 200 cm/hr for the wash with Buffer B (as described above), and then the bound protein eluted with Buffer C (as described above). FIGS. 1, 2 and 3 show the results from contacting a known amount of human Factor VIII to each of the preferred peptide-resins (sequence ID 1, 2 and 3, respectively).

| Sequence ID | Load rhFVIII Total μg | Flow-Through Total μg | Salt Wash Total μg | Elute Total μg |
|---|---|---|---|---|
| 1) WHYYHG | 10 μg | 0.03 | 0.14 | 5.31 |
| 2) HIQHYH | 10 μg | 0.00 | 0.74 | 7.26 |
| 3) HQYGYH | 10 μg | 0.00 | 0.85 | 10.31 |

Recombinant FVIII was applied to each column as described above. The endpoint of this secondary binding assay is to demonstrate binding of the target protein to the preferred peptide ligand; quantification of binding is by the presence or absence of Factor VIII immunological identification (ELISA). ELISA quantitation utilized a polyclonal antisera as capture antibody adsorbed onto the plate well, application of each fraction allowed the Factor VIII to adhere to the capture antibody. The making and using of polyclonal and monoclonal antibodies is well-know, and within the skill of one of ordinary skill in the art. See generally, *Antibodies, A Lab Manual, Harlow and Lane*, eds. 1988 Cold Sprin, Harbor. Then a panel of 3 monoclonal antibodies were used to identify the Factor VIII and detection of these antibodies with a secondary-antibody enzyme conjugate allowed accurate quantitation of the Factor VIII. The flow-through fractions from each injection show greater than 96% target protein depletion by these peptide ligands. The binding avidity was found to be sufficiently strong enough to withstand challenge from high salt buffer wash. The binding avidity was weak enough to permit recovery of target protein during the elution phase of the chromatography.

Demonstration of the binding of FVIII to the peptide resin can also be demonstrated in a radioimmunoassay by radiolabeling the FVIII and measuring the adsorbed and desorbed radioactivity. For instance, $^{14}C$ labeling by reductive methylation using sodium cyanoborohydride and $^{14}C$-formaldehyde is one such technique (see Jentoft et al., Methods in Enzymology 91:570–579 (1983)). It will be apparent to one of ordinary skill in the art that there are other techniques for assessing whether the FVIII has bound to the target peptide, such as fluorometric labeling and analysis, avidin/biotin, etc.

Modification of the six-mer peptides described herein may be made by conservative modifications and substitutions at positions within the peptide (i.e., those that have a minimal effect on the binding of FVIII to the peptide). Such conservative substitutions include those described by Dayhoff in *The Atlas of Protein Sequence and Structure* 5 (1978), and by Argos in EMBO J., 8:779–785 (1989). For example, amino acids belonging to one of the following groups represent conservative changes:

ala, pro, gly, gln, asn, ser, thr;

cys, ser, tyr, thr, val, ile, leu, met, ala, phe;

lys, arg, his;

phe, tyr, trp, his; and asp, glu.

EXAMPLE 1

Preparative hrFVIII Purification by Preferred Peptide Resins.

Preparative batch synthesis of the preferred sequences was performed using 10 g TSK resin (Toyopearl AF-Amino-650M, TosoHaas, Inc., Montgomeyville,. Pa.) as described in Buettner, J., 1996, supra. For each batch, a small amount of resin was loaded into 0.5cm×5cm HPLC columns to demonstrate affinity purification. Three injections of an in-process sample of human Factor VIII were contacted with each resin and fractions of flow-through, salt wash and elution were tested for biological activity, protein profile by SDS-PAGE, and target protein identification by Western blot analyses, as described in Buettner, J., 1996, supra. Biological activity was defined as the ability of the column fraction to reconstitute Factor VIII-depleted plasma to thereby activate Factor X to Factor Xa, with quantitation of enzymatic activity by spectrophotometric measurement of cleaved substrate. (Coatest VIII:C/4, Chromogenix, Molndal, Sweden).

Figure 4:
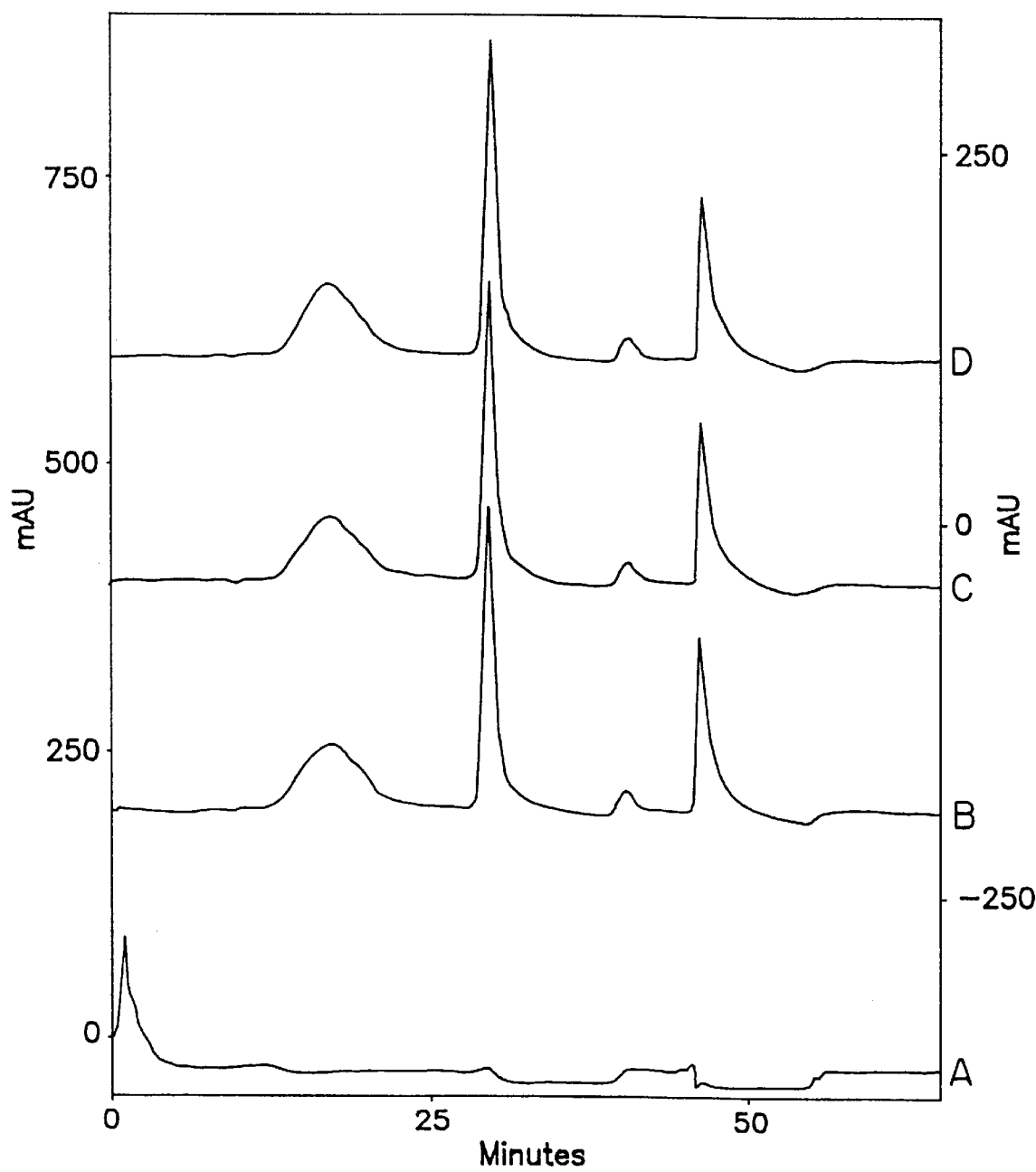
FIG. 4 is a chromatogram showing the overlaid elution profiles (absorbance at 280nm) of chromatographic separations on the peptide WHYYHG-A-TSK650M (SEQ ID NO: 1). A) buffer blank injection with no protein; B) & C) & D) are identical injections of KG2DEAE.
Figure 5:
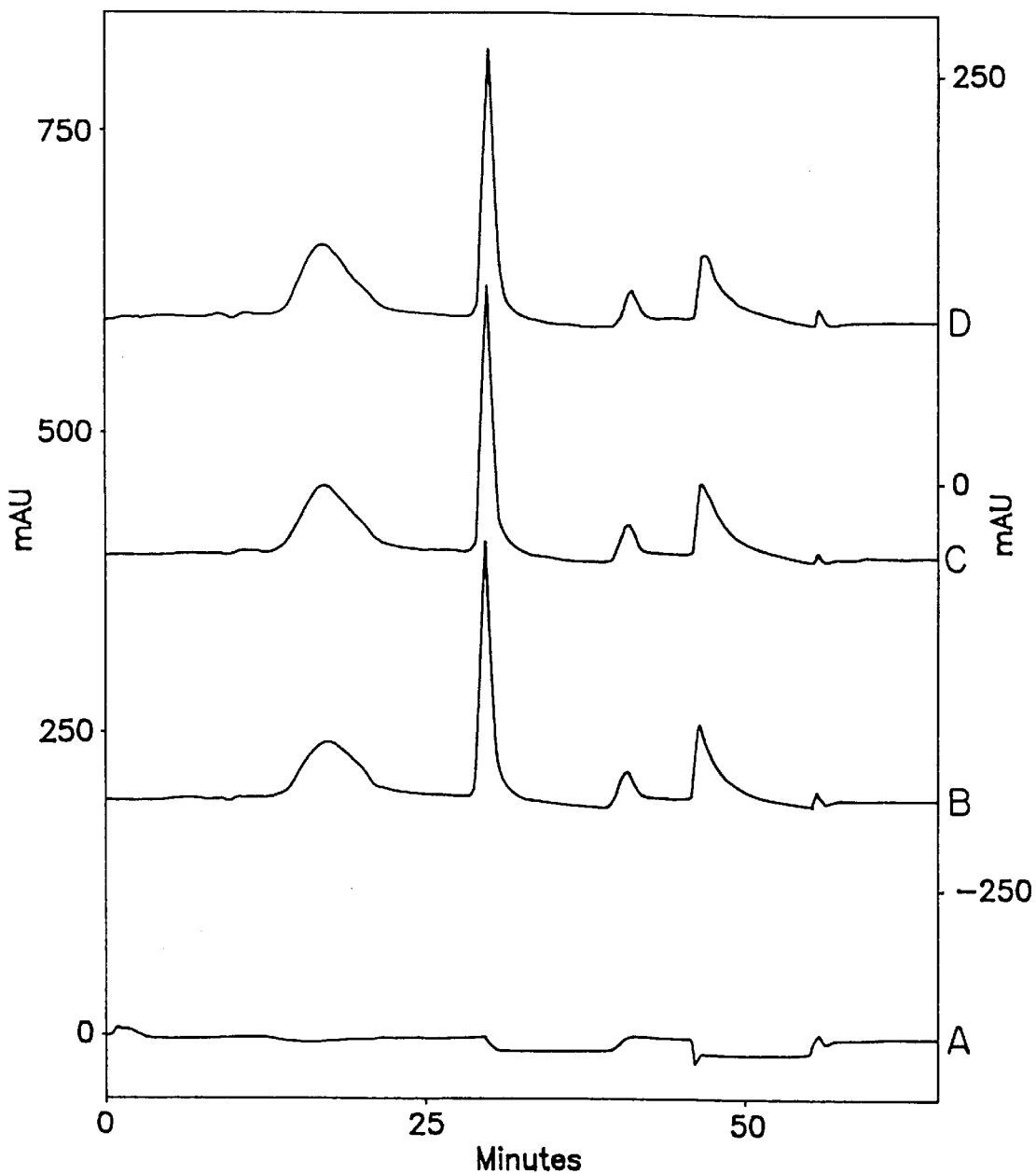
FIG. 5 is a chromatogram showing the overlaid elution profiles (absorbance at 280nm) of chromatographic separations on the peptide HIQHYH-A-TSK650M (SEQ ID NO: 2). A) buffer blank injection with no protein; B) & C) & D) are identical injections of KG2DEAE.
Figure 6:
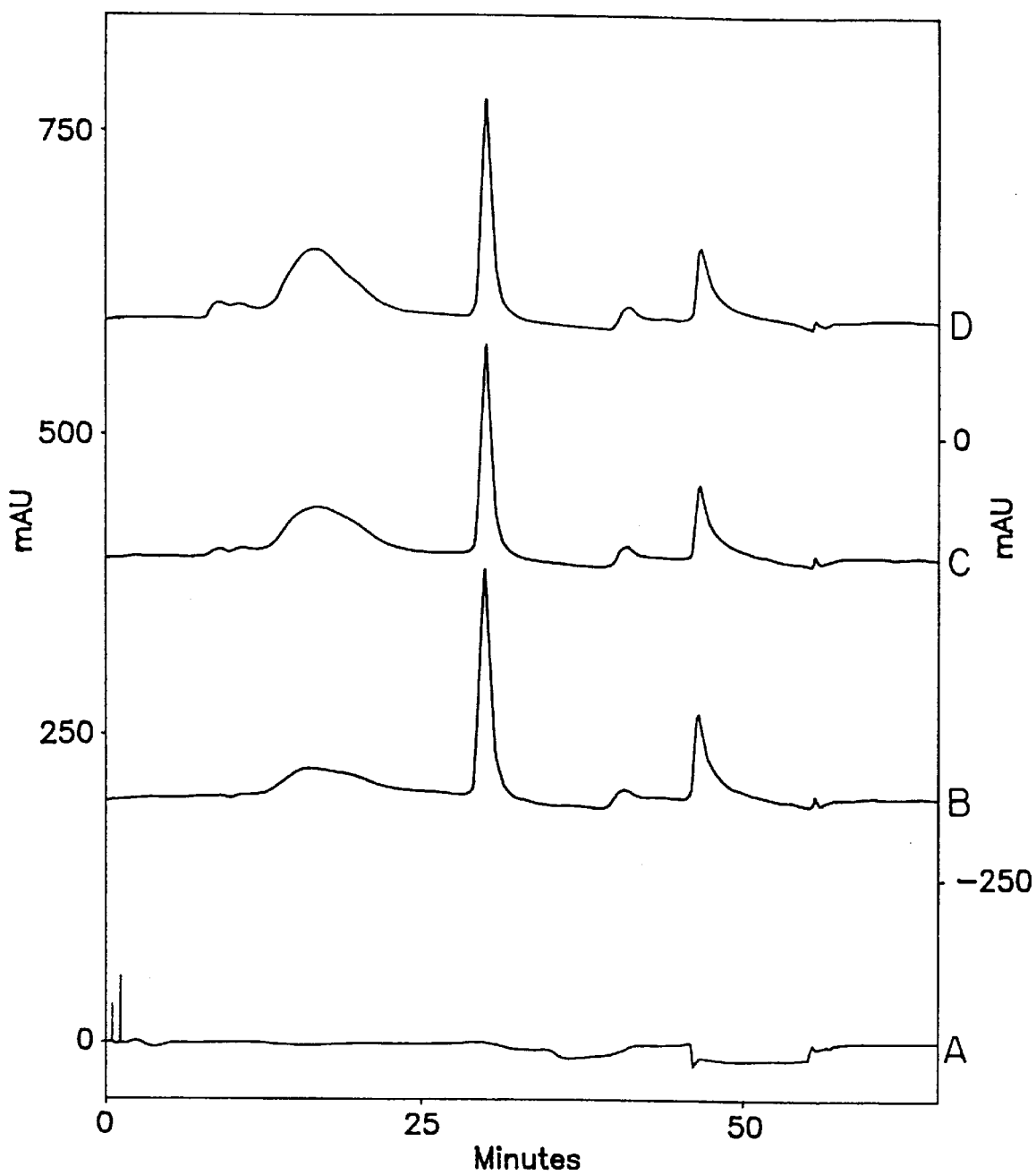
FIG. 6 is a chromatograrn showing the overlaid elution profiles (absorbance at 280nm) of chromatographic separations on the peptide HQYGYH-A-TSK650M (SEQ ID NO: 3). A) buffer blank injection with no protein; B) & C) & D) are identical injections of KG2DEAE.

FIGS. 4, 5 and 6 show the purification chromatograms for binding of the rhFVIII to SEQ IDs 1, 2 and 3, respectively. In each figure, the bottom HPLC trace is the buffer blank injection; the three other HPLC traces are subsequent injections of the KG2DEAE sample. For each chromatogram, flow-through occurs from t=0–22 minutes; salt wash at t26–34 minutes; elution at t=44–54 minutes. Each fraction (flow-through, salt wash and elution) was collected and assayed for Factor VIII activity by the above described Coatest assay.

| Sequence | Load KG2DEAE Total IU | Flow-Through Total IU | Salt Wash Total IU | Elute Total IU | Elute % Recovery | Purification |
|---|---|---|---|---|---|---|
| WHYYHG | | | | | | |
| inj 2 | 136IU | 5IU | 2IU | 35IU | 26% | 1.15 |
| inj 3 | 136IU | 2IU | 2IU | 56IU | 41% | 1.75 |
| inj 4 | 136IU | 6IU | 5IU | 54IU | 40% | 1.64 |
| HIQHYH | | | | | | |
| inj 2 | 136IU | 1IU | 4IU | 42IU | 31% | 1.22 |
| inj 3 | 136IU | 1IU | 7IU | 52IU | 38% | 1.54 |

-continued

| Sequence | Load KG2DEAE Total IU | Flow-Through Total IU | Salt Wash Total IU | Elute Total IU | Elute % Recovery | Purification |
|---|---|---|---|---|---|---|
| inj 4 HQYGYH | 136IU | 1IU | 9IU | 45IU | 33% | 1.48 |
| inj 2 | 136IU | 2IU | 3IU | 62IU | 46% | 1.00 |
| inj 3 | 136IU | 1IU | 3IU | 71IU | 52% | 1.53 |
| inj 4 | 136IU | 1IU | 3IU | 75IU | 55% | 1.47 |

Each of the preferred peptide resins demonstrated quantitative capture of the human Factor VIII applied. As shown in the above data table, each peptide-resin released the biologically competent Factor VIII in the elution fraction under these specific conditions. For each injection of the sample, a purification of 1- to 2-fold was observed.

Figure 7:
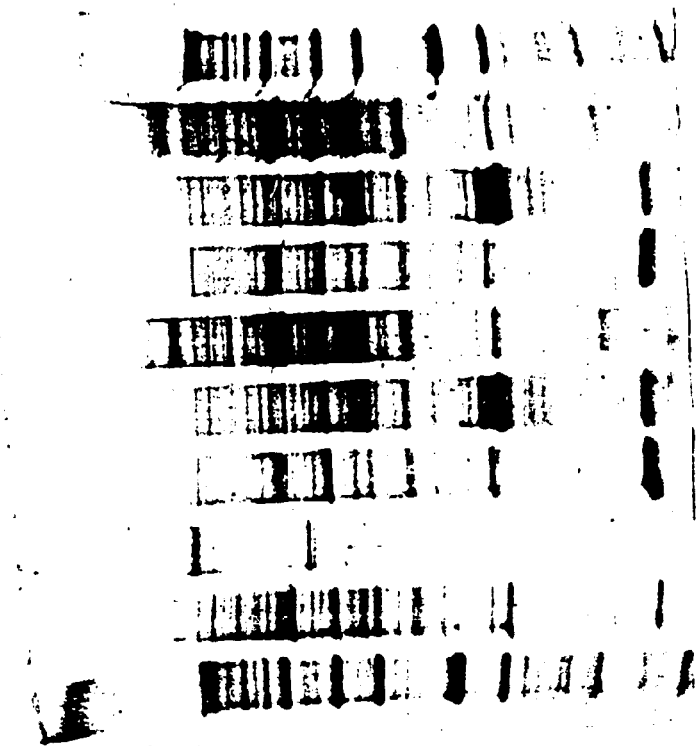
FIG. 7 shows SDS-PAGE and Western Blot analyses for the $2^{nd}$ and 3rd injection for the peptide affinity resin SEQ ID NO: 1 (WHYYHG). Lane designations: M=molecular weight markers; D=KG2DEAE hrFVIII in-process fraction; K=KG2 hrFVIII highly purified; FT=flow-through column fraction; S=salt wash column fraction; E=elution column fraction.
Figure 8:
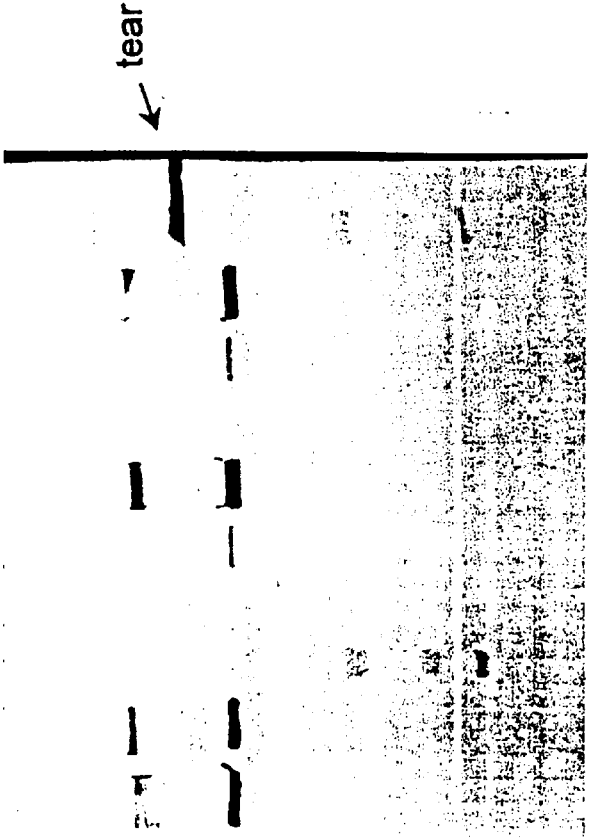
FIG. 8 shows SDS-PAGE and Western Blot analyses for the $2^{nd}$ and $3^{rd}$ injection for the peptide affinity resin SEQ ID NO: 2 (HIQHYH). Lane designations: M=molecular weight markers; D=KG2DEAE hrFVIII in-process fraction; K=KG2 hrFVIII highly purified; FT=flow-through column fraction; S=salt wash column fraction; E=elution column fraction.
Figure 8:
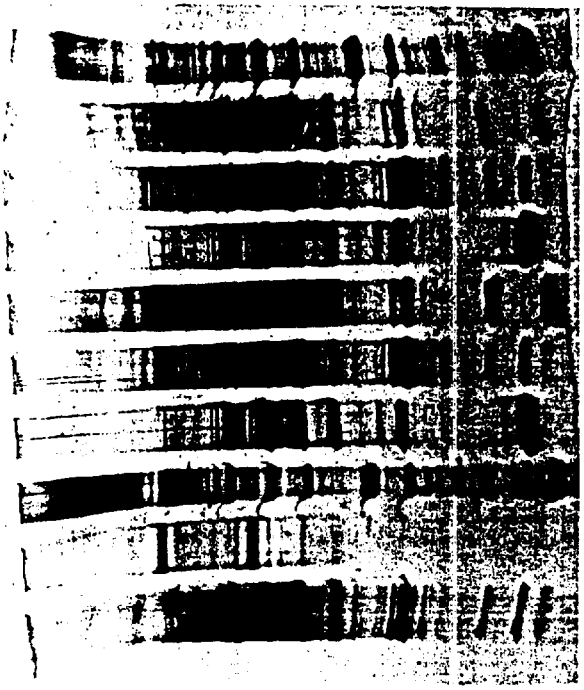
Figure 9:
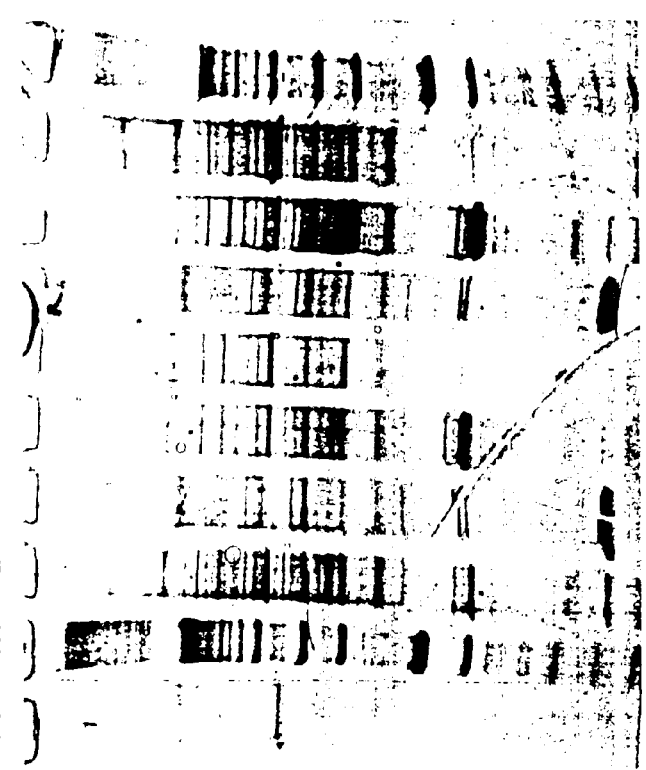
FIG. 9 shows SDS-PAGE and Western Blot analyses for the $2^{nd}$ and $3^{rd}$ injection for the peptide afiity resin SEQ ID NO: 3 (HQYGYH). Lane designations: M=molecular weight markers; D=KG2DEAE hrFVIII in-process fraction; K=KG2 hrFVIII highly purified; FT=flow-through column fraction; S=salt wash column fraction; E=elution column fraction.

FIGS. 7, 8 and 9 show the SDS-PAGE and Western blot profiles for the second and third injection fractions from each of the preferred peptide resins. Each of the SDS-PAGE profiles from the flow-through, salt and elution are consistent within each column run, but are different from the other columns suggesting each resin has a different specificity or selectivity for the sample components. Western blot analyses indicate complete adsorption of the Factor VIII onto each preferred peptide-resin, with preferential release in the elution fraction. Both SDS-PAGE and Western blot analyses confirm the biological assay data presented above.

Other embodiments of the invention will become apparent to one of ordinary skill in the art For instance, minor modifications of the six-mer peptides disclosed herein that substitute, add or delete one or more amino acid residues that are similar in biochemical behavior to those specifically disclosed herein ("conservative substitutions") and that result in similar FVIII binding will be apparent to one of ordinary skill in the art These conservative substitution variants come within the spirit and scope of the invention, as delimited by the claims below.

We claim:

1. A method of purifying Factor VIII comprising the steps of contacting a solution containing Factor VIII with a Factor VIII-binding substrate under conditions sufficient to bind Factor VIII to said substrate, wherein said Factor VIII-binding substrate comprises one or more peptides bound to said substrate, wherein said peptides are selected from the group consisting of SEQ ID NO:1, SEQ ID NO: 2, and SEQ ID NO:3, and then eluting said bound Factor VIII.

* * * * *